(12) United States Patent
McPherson (10) Patent No.: US 8,968,296 B2
(45) Date of Patent: Mar. 3, 2015

(54) ENERGY-HARVESTING SYSTEM, APPARATUS AND METHODS

(71) Applicant: Covidien LP, Mansfield, MA (US)

(72) Inventor: James W. McPherson, Boulder, CO (US)

(73) Assignee: Covidien LP, Mansfield, MA (US)

( * ) Notice: Subject to any disclaimer, the term of this patent is extended or adjusted under 35 U.S.C. 154(b) by 24 days.

(21) Appl. No.: 13/859,084

(22) Filed: Apr. 9, 2013

(65) Prior Publication Data

US 2013/0345695 A1 Dec. 26, 2013

Related U.S. Application Data

(60) Provisional application No. 61/664,546, filed on Jun. 26, 2012.

(51) Int. Cl.
| | |
|---|---|
| A61B 18/10 | (2006.01) |
| A61B 18/12 | (2006.01) |
| A61B 18/18 | (2006.01) |
| H01Q 1/24 | (2006.01) |
| H02J 17/00 | (2006.01) |
| A61B 18/14 | (2006.01) |
| H02J 7/02 | (2006.01) |
| A61B 18/00 | (2006.01) |
| A61B 17/00 | (2006.01) |

(52) U.S. Cl.
CPC ............ *A61B 18/10* (2013.01); *A61B 18/1206* (2013.01); *A61B 18/14* (2013.01); *A61B 18/1815* (2013.01); *H01Q 1/248* (2013.01); *H02J 7/025* (2013.01); *H02J 17/00* (2013.01); *A61B 2018/00928* (2013.01); *A61B 2018/1823* (2013.01); *A61B 2017/00199* (2013.01); *A61B 2017/00411* (2013.01); *A61B 2018/00577* (2013.01); *A61B 2018/00601* (2013.01); *A61B 2018/0063* (2013.01); *A61B 2018/1869* (2013.01); *A61B 2018/1876* (2013.01); *A61B 18/1477* (2013.01)
USPC ............................................... 606/34; 606/41

(58) Field of Classification Search
None
See application file for complete search history.

(56) References Cited

U.S. PATENT DOCUMENTS

| | | |
|---|---|---|
| 6,856,291 B2 | 2/2005 | Mickle |
| 7,024,605 B2 | 4/2006 | Sera et al. |

(Continued)

OTHER PUBLICATIONS

European Search Report dated Oct. 2, 2013 in European Application No. 13173351.

*Primary Examiner* — Michael Peffley
*Assistant Examiner* — Colin Lee (57) ABSTRACT

An electrosurgical energy delivery apparatus includes an energy delivery circuit, a control circuit and an energy-harvesting system with a plurality of energy-harvesting circuits and a voltage regulator that provides a regulated DC voltage to the energy delivery circuit and/or the control circuit. The energy delivery circuit receives an electrosurgical energy signal having a primary frequency and selectively provides the electrosurgical energy signal to an energy delivery element. The control circuit connects to the energy delivery circuit and selectively enables the flow of electrosurgical energy to the energy delivery element. The plurality of energy-harvesting circuits each include an energy-harvesting antenna tuned to a particular frequency, a matched circuit configured to receive an RF signal from the energy-harvesting antenna, rectify the RF signal and generate a DC signal, and an energy storage device that connects to the voltage regulator to receive and store the DC signal.

19 Claims, 8 Drawing Sheets

(56) References Cited

U.S. PATENT DOCUMENTS

| | | |
|---|---|---|
| 7,342,502 B2 * | 3/2008 | Harkins et al. .............. 340/573.1 |
| 7,482,926 B2 * | 1/2009 | Pillai ........................... 340/572.1 |
| 7,528,698 B2 | 5/2009 | Mickle et al. |
| 7,786,867 B2 | 8/2010 | Hamel et al. |
| 7,791,557 B2 | 9/2010 | Mickle et al. |
| 8,362,745 B2 | 1/2013 | Tinaphong |
| 2004/0085247 A1 | 5/2004 | Mickle et al. |
| 2004/0133189 A1 | 7/2004 | Sakurai |
| 2007/0107766 A1 * | 5/2007 | Langley et al. ................ 136/243 |
| 2009/0033465 A1 | 2/2009 | Mickle et al. |
| 2009/0117872 A1 * | 5/2009 | Jorgenson et al. ............ 455/334 |
| 2009/0200985 A1 | 8/2009 | Zane et al. |
| 2010/0130984 A1 | 5/2010 | Ritter et al. |
| 2010/0256710 A1 | 10/2010 | Dinsmoor et al. |
| 2010/0262139 A1 * | 10/2010 | Beller et al. .................... 606/41 |
| 2011/0077719 A1 | 3/2011 | Rofougaran |
| 2011/0130689 A1 * | 6/2011 | Cohen et al. ...................... 601/3 |
| 2012/0139355 A1 | 6/2012 | Ganem et al. |

* cited by examiner

ENERGY-HARVESTING SYSTEM, APPARATUS AND METHODS

CROSS REFERENCE TO RELATED APPLICATION

The present application claims the benefit of and priority to U.S. Provisional Application Ser. No. 61/664,546, filed on Jun. 26, 2012, the entire contents of which are incorporated herein by reference.

BACKGROUND

1. Technical Field

The present disclosure relates generally to harvesting electromagnetic energy for power devices, such as, for example, an electrosurgical energy delivery device used in electrosurgical energy delivery systems for delivering electrosurgical energy to tissue.

2. Background of Related Art

Electrosurgical energy delivery systems and procedures using electrosurgical energy are designed to safely deliver electrosurgical energy to a target tissue. The equipment, the act of energy delivery or the procedures used to deliver energy may be regulated by various governmental or industrial regulations or standards, such as, for example, FCC regulations and standards for medical equipment or electromagnetic compatibility (EMC) regulations and standards to ensure that the electrosurgical equipment does not interfere with other electronic equipment. Industrial standards may be related to patient safety, such as, for example, providing sufficient electrical isolation between a generator and a patient. As such, energy generation and transmission devices are specifically designed to minimize and reduce undesirable energy delivery.

One common practice used to ensure patient safety in electrosurgical generators is to create an isolation barrier between the generator and the patient. For example, patient isolation may be provided by isolating the generator output from an earth ground. Isolation barriers may also be provided by various generally accepted circuits, such as, for example, a transformer or capacitors that would have a low impedance at one or more predetermined frequencies (e.g., 60 Hz).

While the practice of providing an electrical isolation barrier is generally effective with respect to the energy delivery aspect of the system, these techniques, practices and circuits are not as effective in providing isolation between the generator and the DC power circuits and control circuitry in the energy delivery device.

Other means of providing isolation between the generator and the powering control circuitry include providing a delivery device power source in the energy delivery device to independently power the energy delivery device. For example, a battery (or other suitable energy storage device) or a power generation source may be provided to the energy delivery device to provide complete electrical isolation between the generator and the powered control circuitry in the energy delivery device. However, providing a separate power source for the delivery device requires addition of circuitry for charge and/or charge monitoring, circuitry for preventing use when the power source is not functioning properly or not providing an adequate amount of energy for proper operation. In addition, providing an off-the-shelf or custom DC power source or power supply to provide circuit isolation is costly thereby increasing the overall per product costs.

Another system and method for providing DC power for the energy delivery device is to harvest a portion of the energy provided in the isolated energy delivery circuit to provide power to the powered control circuitry in the energy delivery device as taught hereinbelow.

Harvesting of RF energy transmitted through the air for use in powering electronic devices is extremely important in a number of fields, such as radio frequency identification (RFID) systems, security monitoring and remote sensing, among others. For example, RFID systems consist of a number of radio frequency tags or transponders (RFID tags) and one or more radio frequency readers or interrogators (RFID readers). The RFID tags typically include an integrated circuit (IC) chip, such as a complementary metal oxide semiconductor (CMOS) chip, and an antenna connected thereto for allowing the RFID tag to communicate with an RFID reader over an air interface by way of RF signals. In a typical RFID system, one or more RFID readers query the RFID tags for information stored on them, which can be, for example, identification numbers, user written data, or sensed data.

RFID tags are generally categorized as passive tags or active tags. Passive RFID tags do not have an internal power supply. Instead, the electrical current induced in the antenna of a passive RFID tag, by the incoming RF signal from the RFID reader, provides enough power for the IC chip or chips in the tag to power up and transmit a response. One passive tag technology, known as backscatter technology, generates signals by backscattering the carrier signal sent from the RFID reader. In another technology, described in U.S. Pat. Nos. 6,289,237 and 6,615,074, RF energy from the RFID reader is converted to a DC voltage by an antenna/matching circuit/charge pump combination. The DC voltage is then used to power a processor/transmitter/antenna combination that transmits information to the RFID reader at, for example, a different frequency. In either case, the area of the tag or silicon die is valuable, and therefore it is advantageous to make the most efficient use of the space thereon.

Multiple antennas can be used to generate a DC voltage from an RF signal. For example, an RFID tag may use two or more dipole antennas where the greater of the energies produced from one of the two or more dipole antennas is the one that is selected and used. This, however, is not an efficient use of tag space since the energy for the "loser" antenna is not used.

Energy-harvesting circuits, according to some embodiments of the present disclosure employ multiple antennas with each antenna structured to receive an RF signal having an RF frequency range. The RF frequency range for an antenna may be centered about a particular RF frequency or the antenna, or multiple of antennas, may collect energy from a wide range of frequencies. Matching networks and circuitry coupled to each antenna generate a plurality of DC voltage signals and the plurality of voltage signals are combined to create a combined DC voltage signal to power the RFID tag or a transponder.

RFID and/or transducers use various energy-harvesting techniques to identify and/or power a particular device wherein the tag/transducer receives an externally generated and transmitted energy signal. As such, the amount of energy generated by the energy-harvesting circuit is variable and dependant on the strength of the transducer and the distance between the RFID and transducer and transmitted energy signal.

SUMMARY

Embodiments of the presently disclosed microwave antenna assembly are described in detail with reference to the drawing figures wherein like reference numerals identify similar or identical elements. As used herein and as is traditional, the term "distal" refers to the portion that is furthest from the user and the term "proximal" refers to the portion that is closest to the user. In addition, terms such as "above", "below", "forward", "rearward", etc. refer to the orientation of the figures or the direction of components and are simply used for convenience of description.

The term "energy", "electrosurgical energy" and "electrosurgical energy signal" refers broadly to include all types of energy used to treat tissue, e.g., RF energy, ultrasonic energy, microwave energy, thermal energy, light energy, etc. The term "treat" refers to performing a surgical treatment to tissue using energy, e.g. heating, sealing, or energized cutting of tissue and the term "clinical effect" refers to the subsequent results of the treatment.

The present application applies to an electrosurgical system using energy-harvesting technology and techniques from the RFID field, wherein the nature and purpose of the electrosurgical system is to generate and deliver electrosurgical energy to patient tissue. As such, an electrosurgical energy delivery device includes an electrosurgical energy delivery circuit and an energy-harvesting circuit that harvests a sufficient amount of energy from the electrosurgical energy delivery circuit to power and operate one or more functions on the electrosurgical energy delivery device. An electrosurgical system utilizing an energy-harvesting circuit, as described herein, improves patient isolation and furthers patient safety by eliminating a control power connection and communication circuitry connected between the electrosurgical generator and the electrosurgical energy delivery device.

In one aspect of the present disclosure, an electrosurgical energy delivery apparatus includes an energy delivery circuit, a control circuit and an energy-harvesting system. The energy delivery circuit is configured to receive an electrosurgical energy signal from an electrosurgical energy source. The electrosurgical energy signal includes a primary frequency and the energy delivery circuit selectively provides the electrosurgical energy signal to an energy delivery element. The control circuit is operatively connected to the energy delivery circuit and selectively enables the flow of electrosurgical energy to the energy delivery element. The energy-harvesting system includes a plurality of energy-harvesting circuits. Each energy-harvesting circuit includes an energy-harvesting antenna tuned to a particular frequency, a matched circuit, an energy storage device and a voltage regulator. Each matched circuit receives a RF signal, from the corresponding energy-harvesting antenna, at the particular frequency and rectifies the RF signal to generate a DC signal. The energy storage device receives and stores the DC signal and the voltage regulator connects to the energy storage device and provides a regulated DC voltage to the energy delivery circuit and/or the control circuit.

An energy-harvesting circuit may be tuned to the primary frequency of the electrosurgical energy source. Other energy-harvesting circuits may not be tuned to the primary frequency of the electrosurgical energy source.

In another aspect of the electrosurgical energy delivery apparatus, the control circuit further includes a communication circuit configured to provide a wireless connection between the control circuit and the electrosurgical energy source.

In another aspect of the current disclosure, an electrosurgical energy delivery apparatus includes an energy delivery circuit, a control circuit and a control energy-harvesting system. The energy delivery circuit is configured to receive an electrosurgical energy signal, with a primary frequency, from an electrosurgical energy source and selectively provides electrosurgical energy signal to an energy delivery element. The control circuit connects to the energy delivery circuit and selectively enables electrosurgical energy to the energy delivery element. The control energy-harvesting system includes a plurality of energy-harvesting circuits. Each energy-harvesting circuit includes an energy-harvesting antenna tuned to a particular frequency, a matched circuit that receives and rectifies an RF signal from the energy-harvesting antenna at the particular frequency to generate a DC signal and a switch controlled by the DC signal and configured to indicate that the energy-harvesting antenna is receiving the particular frequency. The switch indicates to the control circuit that the particular frequency was received by the energy-harvesting antenna.

In a further aspect of the electrosurgical energy delivery apparatus, the particular frequency of each energy-harvesting circuit is different. In yet a further aspect, the particular frequency of each of the energy-harvesting circuits is not equal to the primary frequency. The electrosurgical energy signal may include energy at a frequency about equal to a particular frequency of any energy-harvesting circuit.

In yet a further aspect of the electrosurgical energy delivery apparatus, the electrosurgical energy signal includes energy at a frequency that corresponds to at least one of the particular frequencies of one of the plurality of energy-harvesting circuits.

In yet another aspect of the current disclosure, an energy-harvesting circuit includes a circuit configured to harvest energy at a first frequency and at a second frequency. The energy harvested at the first frequency generates a DC power signal for powering an electrical control circuit. The energy harvested at a second frequency detects one or more control signals embedded in the electrosurgical energy signal for controlling the electrical control circuit.

BRIEF DESCRIPTION OF THE DRAWINGS

Various embodiments of the present disclosure are described herein with reference to the drawings wherein.

DETAILED DESCRIPTION

The present disclosure is related to systems, methods and apparatuses for generating energy to power electrical devices by harvesting energy from ambient electromagnetic fields. Ambient electromagnetic fields include radiation emitted from cell-phone antennas and towers, Wi-Fi transmitters, high voltage power lines, TV masts and other sources. In one example described herein, harvesting of ambient electromagnetic fields provides power to an electrosurgical device. Power may be utilized for control and/or control power thereby eliminating the need for providing control and/or control power to the electrosurgical device and improving isolation between the patient and the source of electrosurgical energy. The ambient electromagnetic field harvesting described herein may provide energy to power other electrical systems such as remote environmental sensing systems, remote sensing and control devices, wristwatches, wearable electronics, remote wireless hubs and routers and battery powered electronic devices. In some embodiments, the device remains dormant (e.g., asleep and unused) for an extending period of time and the harvested electromagnetic fields provides a continuous supply of energy to charge and/or recharge the energy supply system (e.g., battery, fuel cell, capacitor, etc.).

Figure 1:
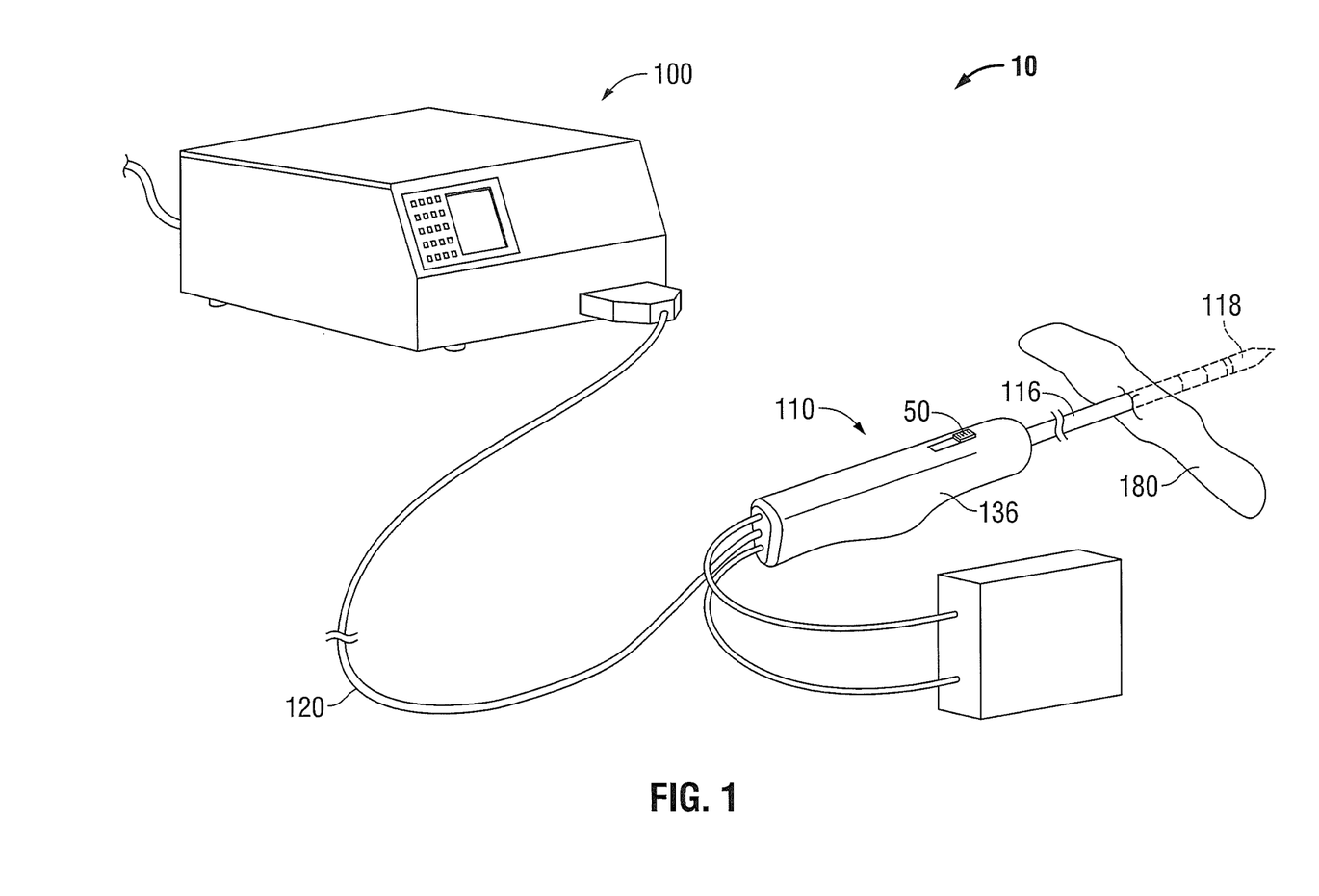
FIG. 1 is a functional block diagram of an electrosurgical energy delivery system according to an embodiment of the present disclosure.

Referring to FIG. 1, an electrosurgical energy delivery system 10 includes an energy delivery device 110 connected to an electrosurgical generator 100 by a transmission line 120. The electrosurgical generator 100 and the corresponding energy delivery device 100 may be configured to delivery an RF energy signal in a RF frequency range or a microwave energy signal in a microwave frequency range. While the embodiments discussed herein are directed to electrosurgical energy signals and harvesting energy from an electrosurgical energy signal, similar harvesting techniques may be used to harvest energy from an electro-mechanical system or mechanical system (e.g., ultrasonic and ultrasonically driven devices) or may be used to harvest energy from an optical system (e.g., laser and/or visible light energy).

The transmission line 120 is configured to convey the energy signal from the electrosurgical generator 100 to the energy delivery device 110. The type of cable used for the transmission line 120 may be selected based on the type of energy signal generated by the electrosurgical generator 100. For example, if the electrosurgical generator 100 and the corresponding energy delivery device 110 are configured to generate and deliver a microwave energy signal, a coaxial cable, or other suitable waveguide, may be selected for the transmission line 120. Similarly, the electrosurgical generator 100 and the corresponding energy delivery device 110 may be configured to generate and deliver a RF energy signal and the transmission line 120 may be any suitable multi-conductor energy delivery cable or coaxial cable. In another embodiment, the transmission line 120 may be configured to transmit an electrical signal to the energy delivery device and the energy delivery device 110 may be configured to convert the electrical signal to a mechanical energy signal that drives a mechanical end-effector (not explicitly shown). In yet another embodiment, the transmission line 120 is an optical wave-guide, such as a fiber optical cable.

As illustrated in FIG. 1, the energy delivery device 110 includes an energy delivery element 118 on the distal end of the energy delivery device 110. As illustrated in FIG. 1, the energy delivery element 118 may form a percutaneous device having a sharpened tip and configured to penetrate tissue on the distal end of a shaft 116 although any suitable energy delivery element 118 may be selected. Energy delivery device 110 may be any suitable medical device configured to receive an electrosurgical energy signal and transfer the electrosurgical energy signal to patient tissue 180. Housing 136 of energy delivery device 110 may house a switch 50 that connects to an energy delivery circuit 110a and/or to a device control circuit 110b (See FIG. 2A). Housing 135 may also house additional control hardware such as additional switches, indicators or operator displays (not explicitly shown).

Figure 2A:
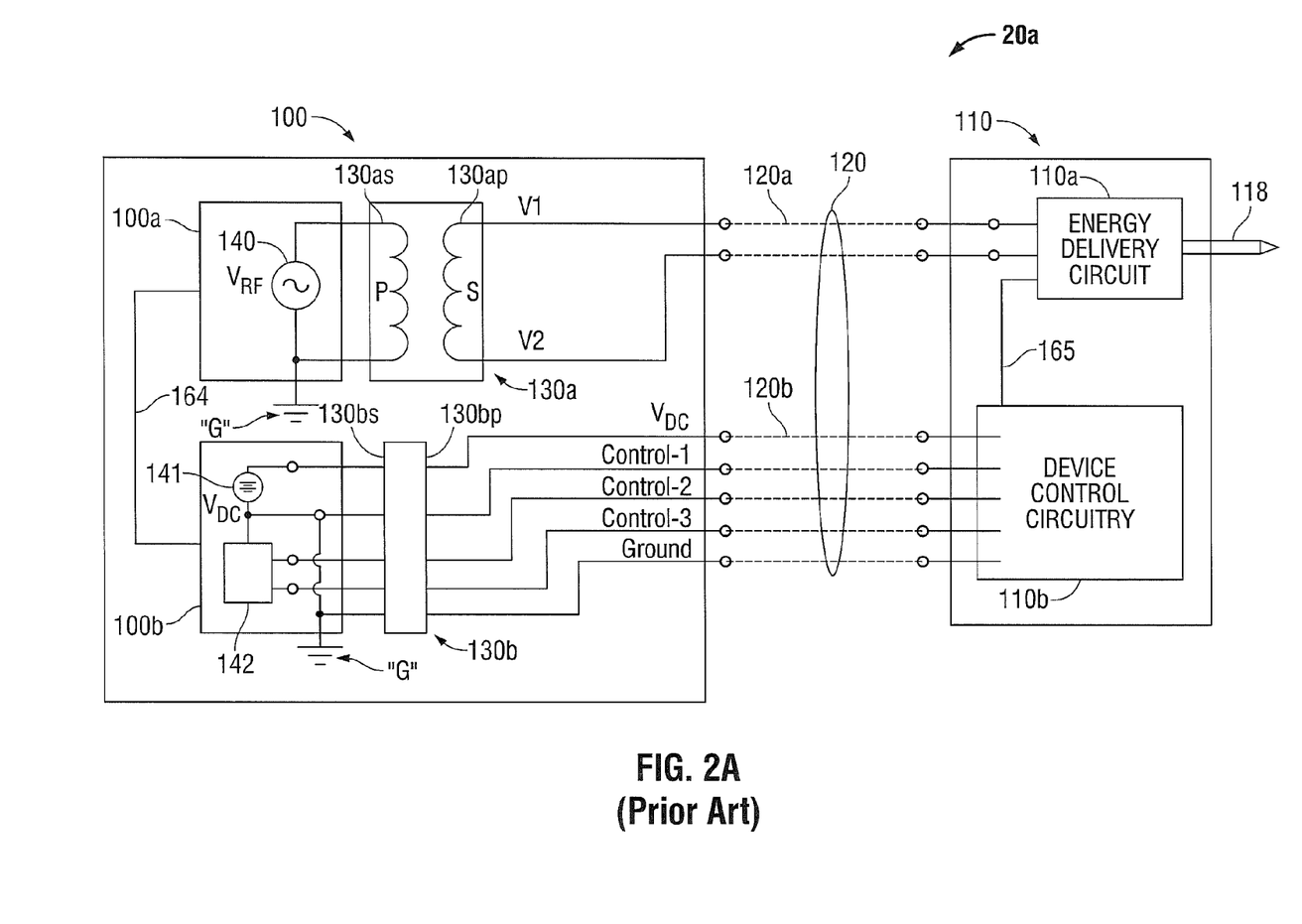
FIG. 2A is an electrical schematic of a conventional electrosurgical energy delivery and control circuit.

FIG. 2A is an electrical schematic of a conventional electrosurgical energy delivery circuit 20a. Electrosurgical energy delivery systems are well known in the art therefore the complete electrical schematic of the electrosurgical energy delivery circuit 20a has been simplified and only includes the portions required to describe the electrosurgical energy delivery system 20a of the present disclosure. The conventional electrosurgical delivery pathway includes the electrosurgical generator circuit 100a and the device energy delivery circuit 110a connected by one or more conductors of the transmission line 120.

The electrosurgical generator circuit 100a includes a signal generator 140 that generates an electrosurgical energy signal $V_{RF}$, a power isolation transformer 130a and a control isolation transformer 130b. One or more generator control signals 164 may pass between the electrosurgical generator circuit 100a and the generator control circuit 100a through the control isolation transformer 130b. Generator control signals 164 may include parameters such as enable/disable, frequency, power, plus duration, pulse width, duty cycle and/or any other necessary or desired control signal.

Electrosurgical energy signal $V_{RF}$ generated by the signal generator 140 includes a primary frequency component wherein the energy of the signal at the primary frequency component generates the desired surgical effect. The primary frequency component may be related to, or selected for, one or more properties of the energy delivery element 118. The power isolation transformer 130a may be any suitable device that transfers energy from a first electrical circuit (microwave energy source $V_{RF}$) to a second electrical circuit (transmission line 120 and energy delivery device 110) without direct electrical contact. The control isolation transformer 130b may be any suitable device that transfers one or more control signals from a first electrical circuit (generator control circuit 100b) to a second electrical circuit (control portion 120b of transmission line 120 and device control circuitry 110b) without direct electrical contact.

Power isolation transformer 130a may include additional circuitry that isolates the electrical circuitry on the generator side (primary 130ap) of the power isolation transformer 130a from the patient side (secondary 130as) of the power isolation transformer 130a. Proper isolation between the generator side (primary 130ap) and the patient side (secondary 130as) is necessary because the equipment, the act of energy delivery and/or the procedures used to deliver energy, are regulated by various governmental or industrial regulations or standards. For example, FCC regulations and standards for microwave equipment or electromagnetic compatibility (EMC) regulations and standards exist to ensure that the microwave equipment does not interfere with other electronic equipment. Additionally, industrial standards related to safety require sufficient electrical isolation between a generator and individuals (e.g., patient and medical staff). Some aspects of the industrial standards limit the amount of stray electrosurgical energy that may be incidentally released during an electrosurgical procedure.

Power isolation transformer 130a and control isolation transform are merely shown as examples of suitable isolation devices that may be used for electrical isolation between the electrosurgical generator 100 and the transmission line 120 that connects to the energy delivery device. Power isolation transformer 130a and control isolation transformer 130b may be replaced with any suitable device that transfers an energy signal from a first electrical circuit (electrosurgical power circuit $V_{RF}$) to a second electrical circuit (energy delivery element 110a of the energy delivery device 110) without direct electrical contact (e.g., by inductive coupling, capacitive coupling, etc. . . . ).

Electrical isolation of electrosurgical devices is provided as an example herein because patient isolation is mandated by FCC regulations in order to provide increased patient safety. Standard state-of-the-art isolation devices simply do not satisfy the stringent FCC requirement for isolation thereby necessitating the development of specific custom isolation systems and/or devices for use therein. As a result, the isolation system/devices used in electrosurgical systems are often custom-designed, expensive and often bulky. As such, elimination of the need to provide a patient isolation circuit for the control signals and/or control power greatly simplifies the electrosurgical systems and reduces costs while providing increased safety by elimination of the need for an isolation system for the control system and/or control power.

Generator control circuit 100b includes a DC power supply 141 that provides DC power to the processor 142 and other parts of the system 20a. For example, DC power supply 141 provides DC power to the device control circuitry 110b of the energy delivery device 110 through a control portion 120b of the transmission line 120. Generator control circuit 100b may also include one or more control signals (e.g., Control-1, Control-2 and Control-3) that connect to the device control circuitry 110b through the control portion 120b of the transmission line 120.

Energy delivery device 110 includes an energy delivery circuit 110a and a device control circuit 110b. Energy delivery circuit 110a receives the electrosurgical energy signal V1-V2 from the patient side (e.g., secondary side 130as) of the power isolation transformer 130a. Energy delivery circuit 110a controls the flow of the electrosurgical energy signal V1-V2 to an energy delivery element 118 that delivers the electrosurgical energy signal V1-V2 to patient tissue.

In one embodiment, the energy delivery element 118 is an ablation element (not explicitly shown) formed on the distal end of the energy delivery device 110. The ablation element may include one or more electrodes configured to deliver electro surgical energy in a monopolar fashion and/or bipolar fashion. Alternatively, ablation element may include an antenna configured to transmit an electro surgical energy signal V1-V2 at a microwave frequency range wherein the ablation element resonates at one or more frequencies.

In another embodiment, the energy delivery element 118 is an end effector (not explicitly shown) formed on the distal end of the energy delivery device 110. End effector may include one or more opposing jaw member pairs (not explicitly shown) configured to seal and cut tissue positioned therebetween or opposing jaw member pairs configured to deliver one or more staples to tissue positioned therebetween. Jaw members may also include one or more electrodes configured to delivery electrosurgical energy in a monopolar fashion and/or a bipolar fashion.

Energy delivery circuit 110a receives one or more control signals 165 from the device control circuit 110b. The device control circuit 110b may provide a control signal 165 that enables and/or disables the flow of electrosurgical energy to the energy delivery element 118. Control signals 165 from the device control circuit 110b may also control one or more features of the electrosurgical energy signal (e.g., voltage, current, power, phase, energy delivery duration, pulse width and/or duration).

To prevent unintended and undesirable transmission of electrosurgical energy to the patient, the power transmission portion 120a and the control transmission portion 120b of the transmission line 120 are electrically isolated from the electrosurgical generator 100.

Figure 2B:
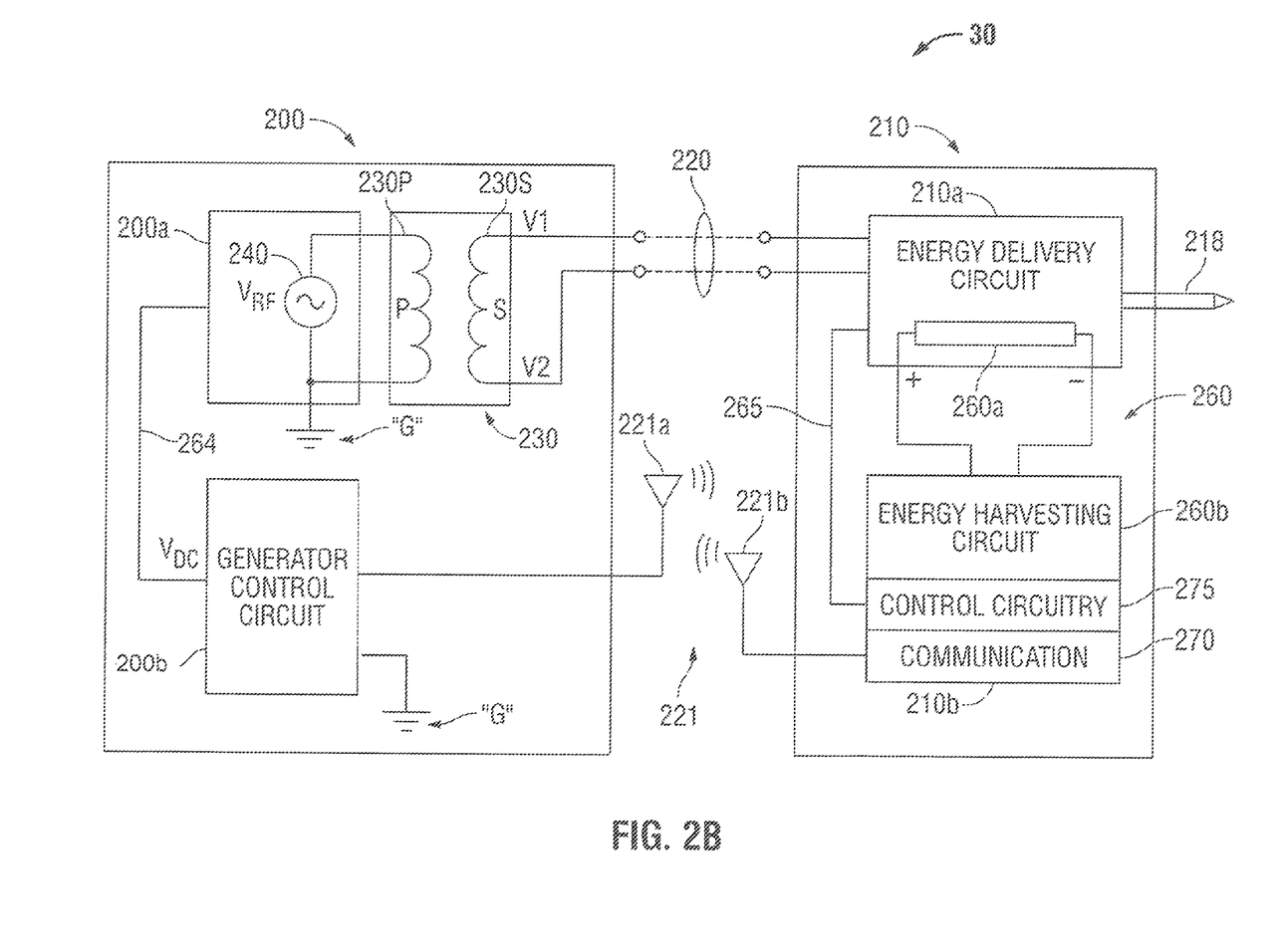
FIG. 2B is an electrical schematic of the electrical harvesting electrosurgical energy delivery system utilizing an energy-harvesting system according to an embodiment of the present disclosure.

FIG. 2B is an electrical schematic of the electrical harvesting electrosurgical energy delivery system 30 utilizing an energy-harvesting system 260 according to one embodiment of the present disclosure. The electrical schematic of the electrical harvesting electrosurgical energy delivery circuit 30 has been simplified and only includes the portions required to describe the electrical harvesting electrosurgical energy delivery system 30 according to the present disclosure. The electrical harvesting electrosurgical energy delivery system includes an electrosurgical generator 200 and an energy-harvesting delivery device 210 wherein the electrosurgical generator 200 only provides an electrosurgical energy signal to the energy-harvesting delivery device 210. The energy-harvesting delivery device 210 harvests energy from any suitable electromagnetic energy signal and is configured to generate a DC power signal for use in the energy-harvesting delivery device 210.

The electrosurgical energy signal pathway includes an electrosurgical power circuit 200a and a device energy delivery circuit 210a connected by one or more conductors in the transmission line 220. The electrosurgical power circuit 200a includes a generator 240 and an isolation transformer 230. The generator 240 generates the electrosurgical energy signal $V_{RF}$. The power isolation transformer 230, which functions similarly to the power isolation transformer 130a discussed hereinabove with respect to FIG. 2A, isolates the electrosurgical power circuit 200a from the transmission line 220 and the device energy delivery circuit 210a.

As discussed hereinabove with respect to power isolation transformer 130a, isolation transformer 230 is shown merely as an example of a suitable generator isolation device. Generator isolation transformer 230 may be any suitable device that transfers an energy signal $V_{RF}$ from a first electrical circuit (electrosurgical power circuit 200a) to a second electrical circuit (transmission line 220 and device energy delivery circuit 210a of the energy-harvesting delivery device 210) without a direct electrical contact, such as, for example, by inductive coupling or capacitive coupling.

Generator control circuit 200b provides one or more control signals to the electrosurgical power circuit 200a. In one embodiment, the generator control circuit 200b provides the control signals to the device control circuit 210b of the energy-harvesting delivery device 210 via a wireless communication network 221. Wireless communication network 221 includes a generator transceiver 221a and a device transceiver 221b. The wireless communication network 221 eliminates direct electrical connections for the transfer of control information between the generator control circuit 200b and the device control circuit 210b of the energy-harvesting delivery device 210.

In another embodiment, the electrosurgical power circuit 200a receives an information signal from the generator control circuit 200b. The information from one or more information signals may be integrated into, or combined with, the electrosurgical energy signal that is provided to the device energy delivery circuit 210a. The electrosurgical energy signal may be utilized as a carrier signal for the information wherein the information is extracted by the device energy delivery circuit 210a. The information may also be represented within the electrosurgical energy signal by adding one or more signals to the electrosurgical energy signal. The one or more signals added to the electrosurgical energy signal include energy at one or more pre-selected frequencies wherein the one or more of the pre-selected frequencies correspond to frequency F1-F4 of an energy-harvesting system 260 (See FIGS. 3-5, 256, 356a-356d and 456a-456d).

Other means of communication may be used to provide an indirect communication link between the generator control circuit 200b and the device control circuit 210b.

Energy-harvesting delivery device 210 includes a device energy delivery circuit 210a and a device control circuit 210b. Device energy delivery circuit 210a receives the electrosurgical energy signal V1-V2 from the patient side (secondary side 230S) of the isolation transformer 230. Device energy delivery circuit 210a controls the flow of the electrosurgical energy signal V1-V2 to an energy delivery element 218 that delivers at least a portion of the electrosurgical energy signal to patient tissue.

As discussed hereinabove with respect to FIG. 2A, the energy delivery element 218 may be an ablation element configured to delivery electrosurgical energy (e.g., one or more electrodes arranged in a monopolar or bipolar fashion and/or an antenna configured to transmit the electrosurgical energy signal V1-V2 at a microwave frequency range). Energy delivery element 218 may include an end effector formed on the distal end of the energy-harvesting delivery device 210 (e.g., one or more opposing jaw member pairs configured to seal and/or cut tissue positioned therebetween or configured to deliver one or more staples to tissue positioned therebetween).

Energy-harvesting delivery device 210 also includes an energy-harvesting system 260 according to embodiments of the present disclosure. Energy-harvesting system 260 includes a harvesting array 260a and a harvesting control circuit 260b. Harvesting array 260a is configured to harvest energy from any suitable electromagnetic signal such as, for example, any unregulated or regulated electromagnetic signal. Examples of unregulated frequencies in the United States include electromagnetic signals with a frequency of about 13.56 MHz, electromagnetic signals between about 902 MHz and about 928 MHz, electromagnetic signals with a frequency of about 2.4 GHz, electromagnetic signals between about 4 GHz and about 6 GHz, and electromagnetic signals between about 21 GHz and about 23 GHz. Unregulated frequencies vary from country to country and may occupy different frequency bands.

Examples of regulated frequencies include frequencies allocated for use with specific devices and systems such as mobile phones, cordless home phones, garage door openers, car key remote control, broadcast television and audio, standard time broadcast, radar (e.g., vehicle-speed, air traffic and weather), mobile radio, Global Positioning System (GPS) navigation, satellite TV broadcast, microwave ovens, Bluetooth, Wifi, Zigbee, RFID devices (e.g., active badges, passports, wireless gasoline tokens, no-contact credit-cards, and product tags), toll-road payment vehicle transponders, radio controlled devices (e.g., model aircraft and vehicles) and wireless microphones and musical instruments.

The abundance and availability of regulated and unregulated signals at various frequencies provides the energy-harvesting system 260 with many available sources of energy. In some embodiments, the harvesting array 260a may be included in (e.g., proximal to) the device energy delivery circuit 210a and may be configured to harvest energy from the electrosurgical energy signal. In other embodiments, harvesting control circuit 260b may be part of, or formed in, the device control circuit 210b or may be a separate circuit and configured to harvest energy from any one or more regulated or unregulated frequency bands. Harvesting control circuit 260b receives harvested energy from the harvesting array 260a and converts at least a portion of the harvested energy into a power signal to power the remaining portion of the device control circuit 210b (e.g., control circuitry 275 and/or communication circuitry 270).

In some embodiments, harvesting control circuit 260b may be configured to harvest regulated and unregulated signals from free space and therefore need not be proximal to any portion of the electrosurgical energy transmission system. The energy contained in the regulated and unregulated signals and ambient electrical noise signals and harvested by the harvesting control circuit 260b would otherwise be wasted energy. Harvesting control circuit 260b collects the unused energy and converts the collected energy to a usable energy state (e.g., DC voltage).

In some embodiments, harvesting array 260a may be configured to harvest information from the electrosurgical energy signal. For example, information may be obtained from the intensity and/or phase of one or more of the harvested signals at a frequency or in a frequency range. Information may also be obtained or extracted from the intensity, phase and/or ratio between two or more harvested signals.

The device control circuit 210b receives a regulated DC power signal from the harvesting control circuit 260b. Device control circuit 210b provides one or more control signals 265 to the device energy delivery circuit 210a. Communication circuit 270 of the device control circuit 210b may provide one or more information signals and/or control signals to the generator control circuit 200b via the device transceiver 221b and generator transceiver 221a of the wireless communication network 221.

Energy delivery circuit 210a receives one or more control signals 265 from the device control circuit 210b. The device control circuit 210b may provide, as one signal of the control signals 265, a signal that enables and/or disables the flow of electrosurgical energy to the energy delivery element 218. For example, in one embodiment the device control circuit 210b may provide, via the control signals 265, a DC signal that selectively enables/disables the energy delivery circuit 210a that selectively provides the electrosurgical energy signal to the energy delivery element 218. Control signals 265 from the device control circuit 210b may also control one or more features of the electrosurgical energy signal (e.g., voltage, current, power, phase, energy delivery duration, pulse width and/or duration).

Figure 3:
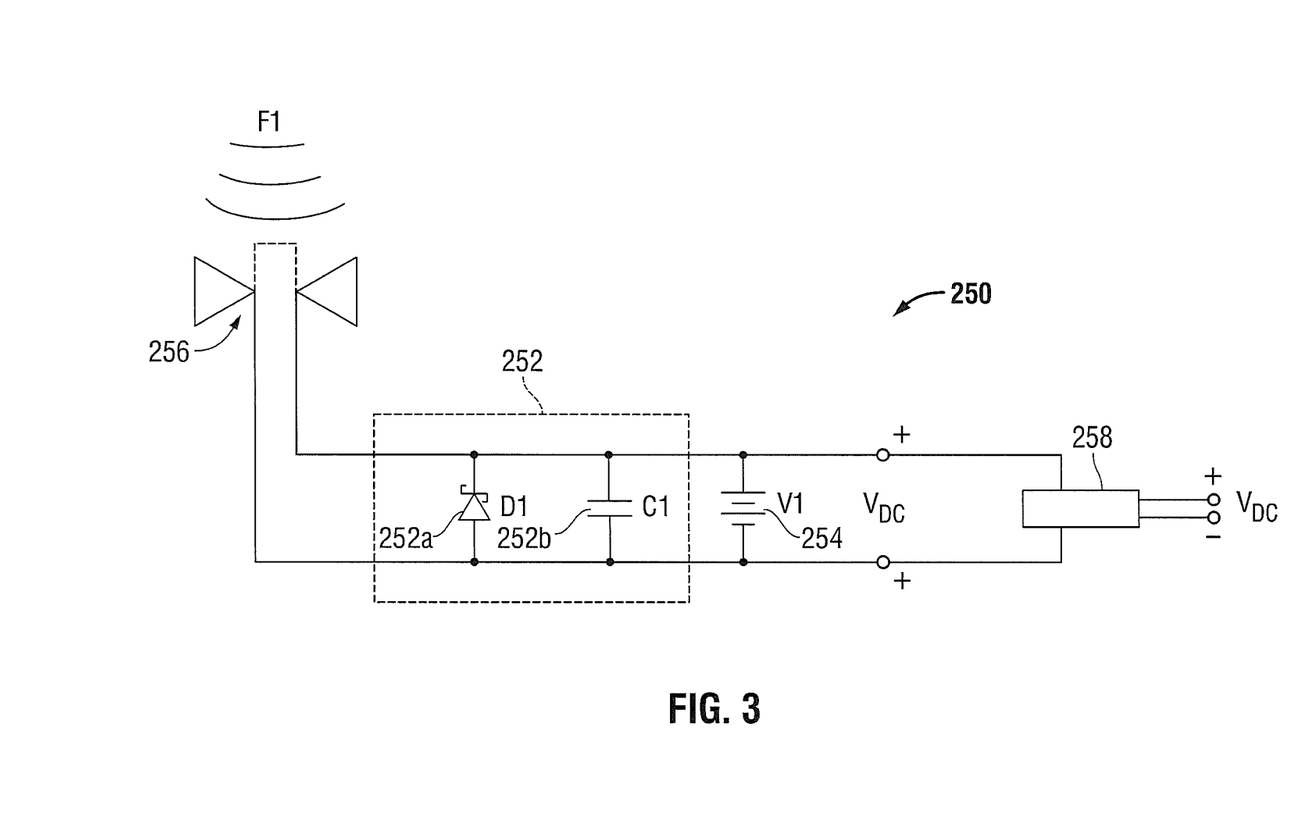
FIG. 3 is an electrical schematic of a harvesting circuit according to an embodiment of the present disclosure.

FIG. 3 is a simplified electrical schematic of a rectifying antenna energy-harvesting circuit 250 (rectenna 250) according to an embodiment of the present disclosure. The rectenna 250 may be used in, or as part of, the energy-harvesting system 260 illustrated in FIGS. 2B and 4-7. Rectenna 250 includes an energy-harvesting antenna 256, a matched circuit 252, an energy storage device (e.g., battery 254) and a voltage regulator 258. The rectenna 250 harvests energy at a first frequency F1, converts the energy to a rectified DC signal, stores at least a portion of the rectified DC signal and converts the rectified DC potential to a regulated DC power output $V_{DC}$.

Energy-harvesting antenna 256 is operatively coupled to a matched circuit 252. The energy-harvesting antenna 256 and the matched circuit 252 are tuned to first frequency F1, wherein the energy-harvesting antenna 256 responds to the first frequency F1 and generates an electrical signal that is provided to the matched circuit 252. Matched circuit 252 includes a rectifier D1 252a and a capacitor C1 252b that are impedance matched to the energy-harvesting antenna 256 at the first frequency F1 and adapted to generate a rectified DC signal from the signal provided by the energy-harvesting antenna 256. The rectified DC signal is provided to the energy storage device (e.g., battery 254).

The rectifier D1 252a is illustrated in FIGS. 3-7 as a Schottky Diode. Rectifying circuits are well known in the art and any suitable rectifying circuit may be utilized. Rectifier D1 252 a may couple to the capacitor C1 252b for short term storage, may couple to a battery 254 for long term storage or may couple to a capacitor C1 252b and a battery 254 for short and long term storage, as illustrated herein.

Matched circuit 252 may also include a charge pump, or similar amplification circuit, that amplifies the electrical signal from the energy-harvesting antenna 256 thereby providing an amplified signal to the energy storage device (e.g., battery 254). Charge pumps are well known in the art and may include one or more amplification stages.

Voltage regulator 258 is configured to provide a regulated voltage output $V_{DC}$ to the device energy delivery circuit 210a and/or the device control circuitry 210b of the energy-harvesting delivery device 210 illustrated in FIG. 2B.

In some embodiments, the energy-harvesting antenna 256 is a wideband, multiband and/or broadband antenna, having a frequency range, capable of receiving energy signals from the frequency range. The frequency range may be selected for the availability of regulated and unregulated frequencies and/or selected for energy patterns in ambient noise.

One specific antenna is a fractal antenna. Fractal antennas are compact multiband and/or wideband antennas capable of receiving energy signals within a frequency range of the fractal antenna. Fractal antennas may also be configured to receive energy signals at specific frequencies with the frequency range of the fractal antenna.

Figure 4:
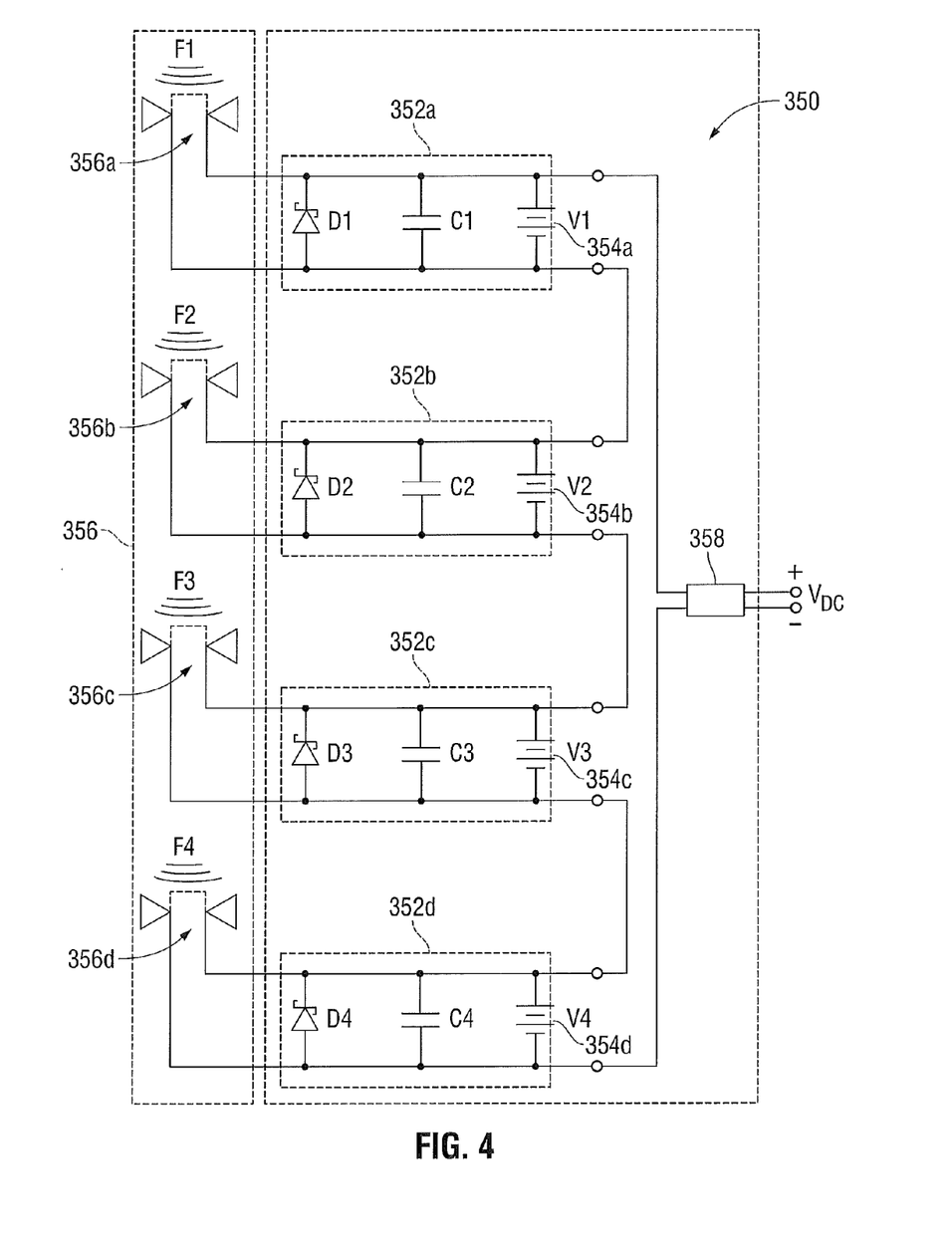
FIG. 4 is an electrical schematic of an energy-harvesting system including an energy-harvesting array and an energy-harvesting control circuit according to an embodiment of the present disclosure.
Figure 5:
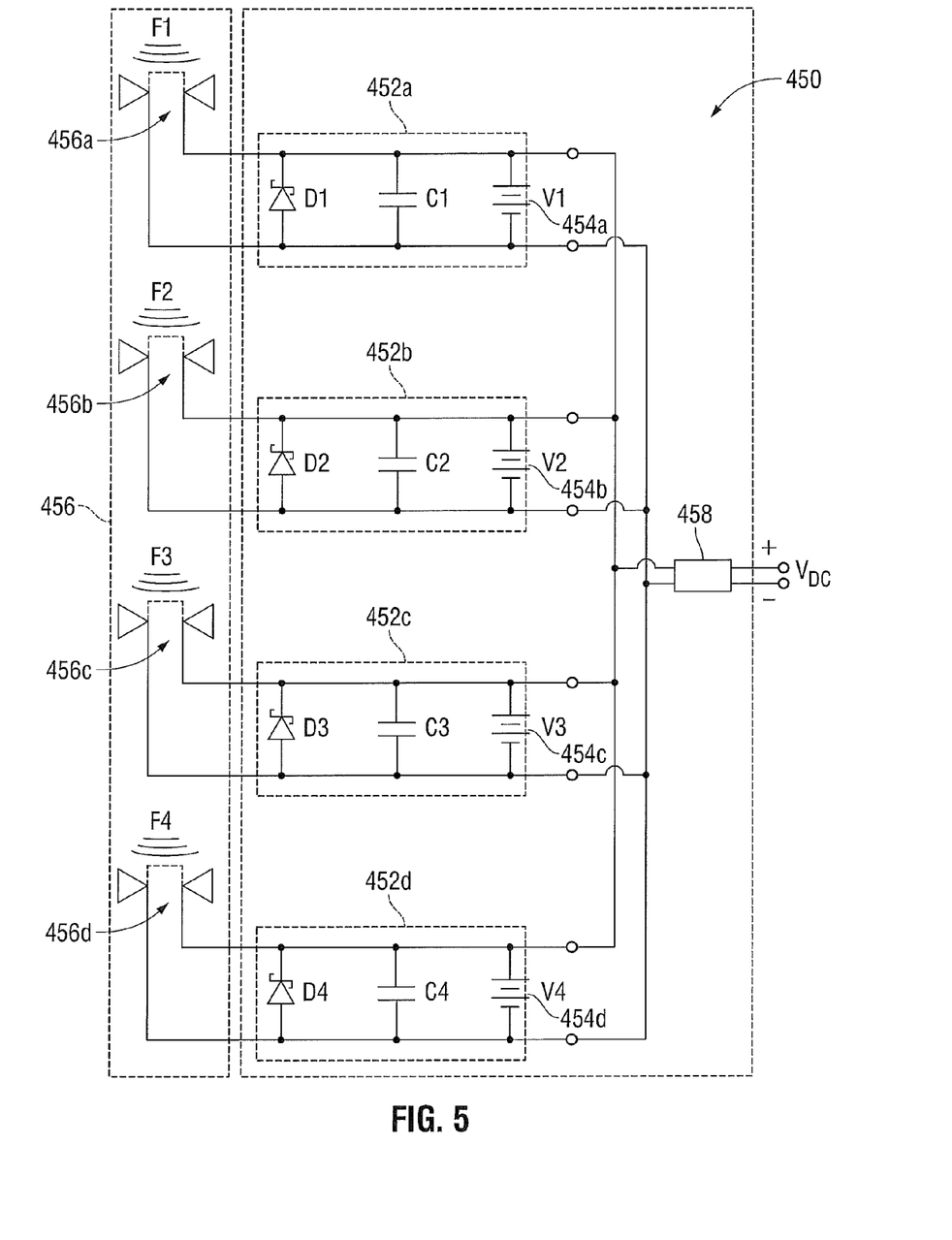
FIG. 5 is an electrical schematic of an alternative circuit of an energy-harvesting system including an energy-harvesting array and an energy-harvesting control circuit according to another embodiment of the present disclosure.

FIGS. 4 and 5 are electrical schematics of energy-harvesting circuits 350, 450 including an energy-harvesting array 356, 456 with corresponding matched circuits 352, 452 and energy storage devices (e.g., batteries 354, 454). In FIG. 4, the storage devices (e.g., batteries 354) are wired as a series circuit and connected to the voltage regulator 358, which generates a regulated voltage output $V_{DC}$ therefrom. In FIG. 5, the storage devices (e.g., batteries 454) are wired as a parallel circuit and connected to the voltage regulator 458 and the voltage regulator 458 that generates a regulated voltage output $V_{DC}$ therefrom.

In FIG. 4, each of the energy-harvesting antennas 356a-356d, and the corresponding matched circuit 352a-352d, are matched to a frequency F1-F4. More specifically, energy-harvesting antenna 356a and matched circuit 352a are matched to a first frequency F1. Energy-harvesting antenna 356b and matched circuit 352b are matched to a second frequency F2. Energy-harvesting antenna 356c and matched circuit 352c are matched to a third frequency F3. Finally, energy-harvesting antenna 356d and matched circuit 352d are matched to a fourth frequency F4. The frequencies F1-F4 may be a specific frequency or a specific frequency range.

In FIG. 5 each of the energy-harvesting antennas 456a-456d, and the corresponding matched circuit 452a-452d, are matched to a frequency F1-F4. More specifically, energy-harvesting antenna 456a and matched circuit 452a are matched to a first frequency F1. Energy-harvesting antenna 456b and matched circuit 452b are matched to a second frequency F2. Energy-harvesting antenna 456c and matched circuit 452c are matched to a third frequency F3. Finally, energy-harvesting antenna 456d and matched circuit 452d are matched to a fourth frequency F4.

FIGS. 4 and 5 each illustrate an energy-harvesting antenna array 356, 456 that include four (4) energy-harvesting antennas 356a-356d, 456a-456d with corresponding matched circuits 352a-352d, 452a-452d tuned to frequencies F1-F4. The energy-harvesting circuit 350, 450 may include any number of antennas, with corresponding circuitry, each tuned to a frequency and/or frequency range.

An energy-harvesting system 260 including an energy-harvesting antenna array 356, 456 and/or the individuals circuits contained therein may harvest energy from a variety of sources, may harvest energy from the same source or any combination thereof. Each source may include one or more frequencies and may provide energy to one or more of the energy-harvesting antennas 356a-356d, 456a-456d.

In one embodiment, the energy-harvesting antenna array 356, 456 is tuned to harvest energy at a frequency equal to the primary frequency that generates the desired surgical effect. As such, the energy-harvesting system 260 is configured to harvest a portion of the energy provided for generating the desired surgical effect during energy delivery. Energy-harvesting system 260 may also be configured to harvest leakage energy when the energy-harvesting delivery device 210 is not providing the surgical effect thereby decreasing the amount of leakage energy transmitted by the energy-harvesting delivery device 210.

In another embodiment, one or more of the antennas in the energy-harvesting antenna array 356, 456 are tuned to harvest energy from noise (e.g., system noise and/or ambient noise). As such, the energy-harvesting system 260 of the energy-harvesting delivery device 210 may provide a periodic trickle charge to one or more storage devices (e.g., batteries 354a-354d, 454a-454d).

In yet another embodiment, one or more of the antennas 356a-356d, 456a-456d in the energy-harvesting antenna array 356, 456 is tuned to a frequency generated as an undesirable byproduct or result of the delivery of energy by the energy-harvesting delivery device 210. For example, an energy-harvesting delivery device 210 configured to generate a surgical effect with a microwave energy signal may generate undesirable energy at odd harmonics frequencies of the primary frequency. The energy-harvesting antenna array 356, 456 may include one or more antennas tuned to harvest the undesirable energy at these harmonic frequencies thereby decreasing the leakage that would have otherwise occurred due to harmonic generation.

The energy-harvesting antenna array 356, 456 may harvest energy from a wide range of frequencies. Frequencies may be selected to maintain battery power by generating a trickle charge, frequencies may be selected to generate energy during operation of the device, frequencies may be selected to reduce undesirable leakage energy, thereby increase patient safety of the devices, or any combination thereof.

Energy-harvesting antennas 356a-356d and 456a-456d may be configured to harvest energy over a wide range of frequencies. For example, each frequency F1-F4 may include a range of frequencies and each range of frequencies may include overlapping portions thereof. As such, an energy-harvesting delivery device would allow for collection of ambient RF fields, the primary frequency generated by the electrosurgical power circuit 200a, as well as low-level energy associated with switching power supplies, microprocessor clocks and ambient noise.

Energy-harvesting delivery device 210 is capable of capturing, harvesting and storing energy from ambient or stray electronic signals that would have been otherwise been unused. As such, the energy-harvesting delivery device 210 is capable of maintaining and regaining energy without receiving energy from an external power source.

Figure 6:
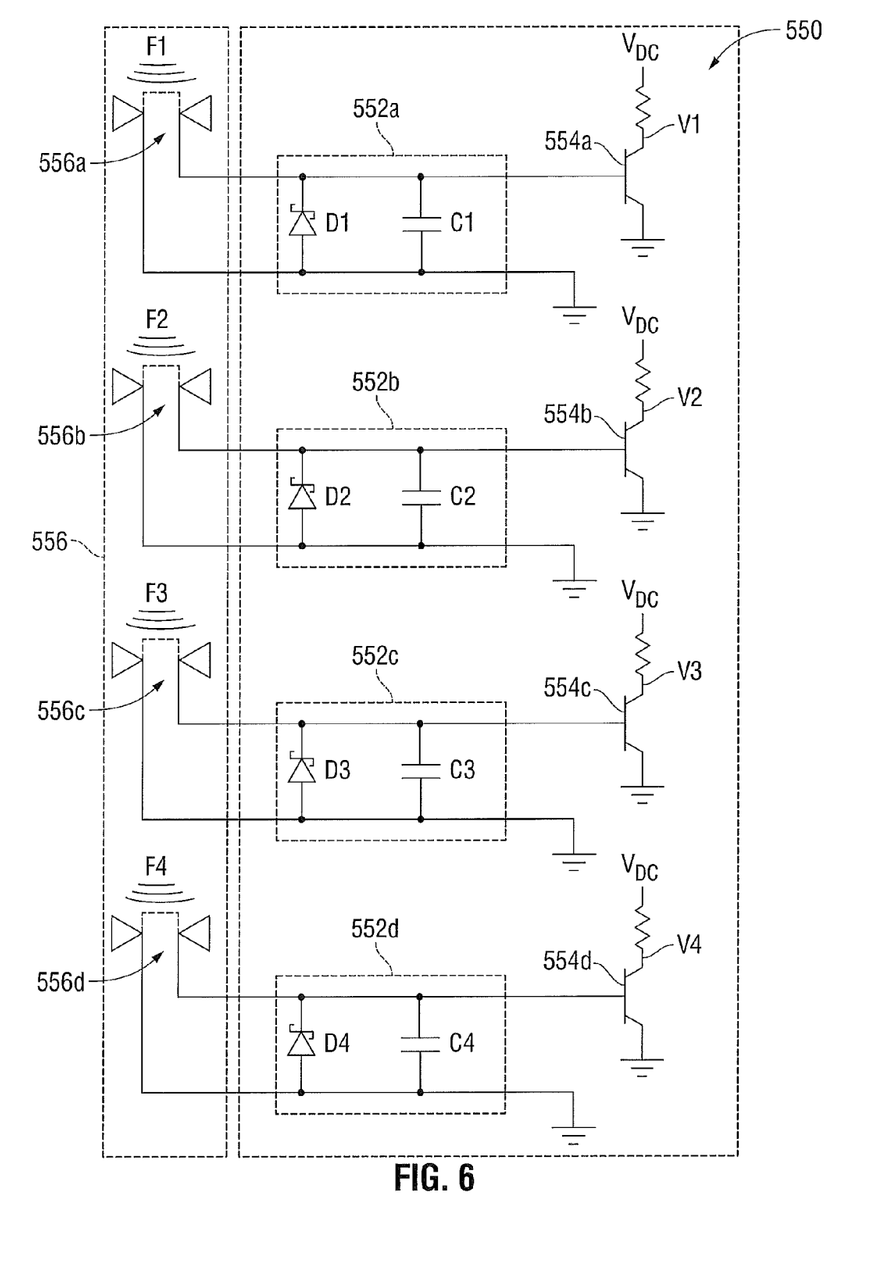
FIG. 6 is an electrical schematic of a control harvesting circuit configured to harvest control information from an electrosurgical energy signal according to another embodiment of the present disclosure.

FIG. 6 is an electrical schematic of a control harvesting circuit 550 configured to harvest control information from an electrosurgical energy signal according to another embodiment of the present disclosure. Control harvesting circuit 550 includes an energy-harvesting array 556 and matched circuits 552 similar to the energy-harvesting arrays 356, 456 and matched circuits 352, 452 of FIGS. 4 and 5. Each individual output of the matched circuit 552a-552d provides a corresponding gate signal to a corresponding control transistor 554a-554d. Gating the control transistor 554a-554d transitions the corresponding control signal V1-V4 from $V_{DC}$ to ground.

In use, each antenna 556a-556d is tuned to a frequency or frequency range wherein exposure to a signal with the tuned frequency or frequency range excites the antenna thereby generating energy. With reference to FIG. 2B, the generator control circuit 200b provides one or more control signals to the generator 240. The generator 240 generates an electrosurgical energy signal at a primary frequency for generating a desired clinical effect. Additionally, the generator 240, if instructed, adds to the electrosurgical energy signal one or more additional signals with energy at one or more frequencies or frequency ranges that correspond to the frequency F1-F4 of one or more of the antenna 556a-556d.

The electrosurgical energy signal is provided to the device energy delivery circuit 210a via the transmission cable 220. The corresponding antennas 556a-556d tuned to the frequencies F1-F4 of the one or more addition signals (as instructed by the control signals from the generator control circuit 200b) harvest energy from the energy signal and provide the harvested energy to the corresponding matched circuit 552a-552d. The signal provided to one or more of the matched circuits 552a-552d builds a charge on the corresponding capacitor C1-C4. When the voltage on the capacitor exceeds the gate voltage of the corresponding transistor 554a-554d the transistor opens and the voltage on the control signal V1-V4 transitions from VDC to ground. The control signals V1-V4 are provided to the control circuitry 275 of the device control circuit 210b thereby providing the control information from the electrosurgical generators 200 to the energy-harvesting delivery device 210.

Figure 7:
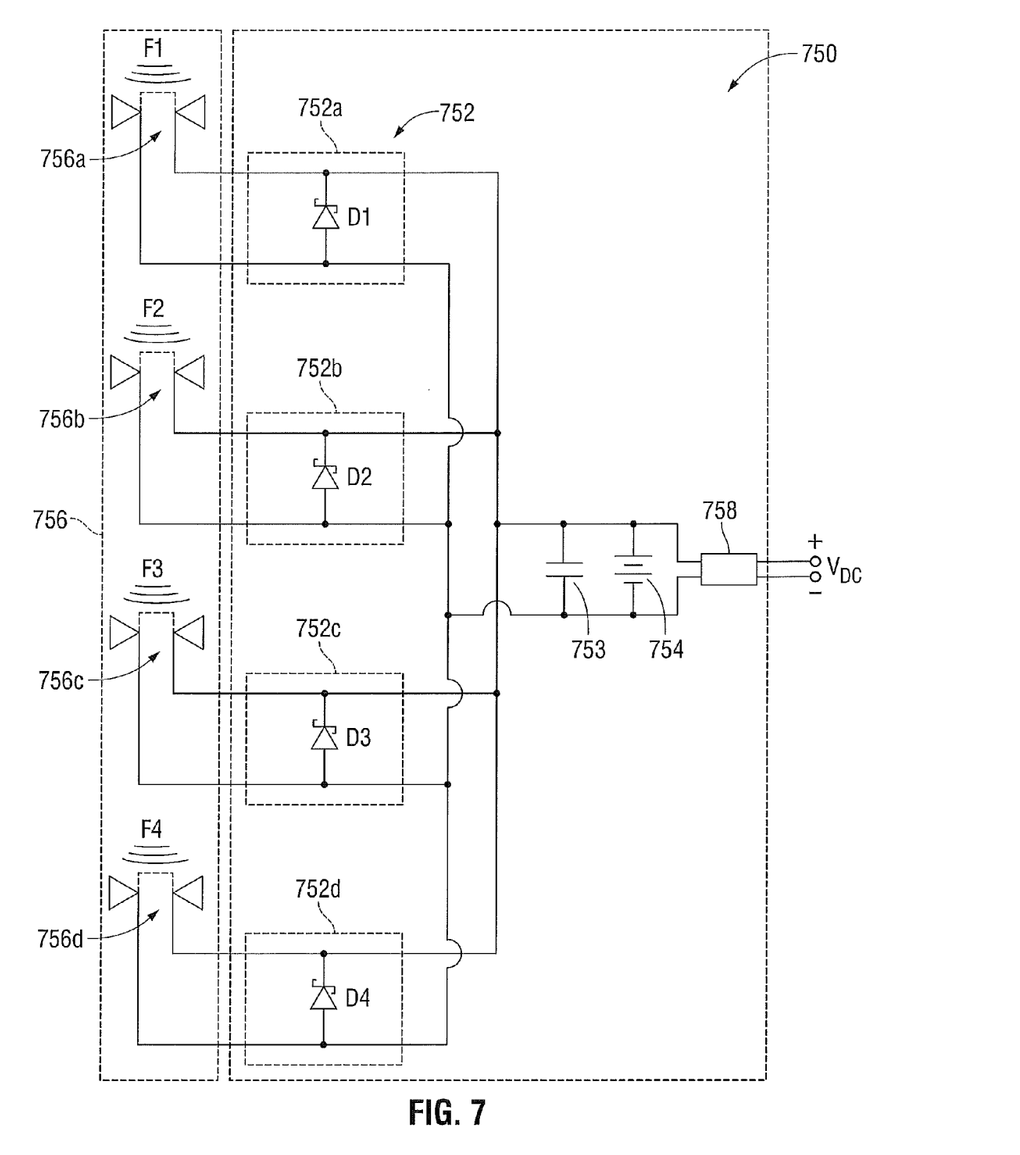
FIG. 7 is an electrical schematic of yet another energy-harvesting system including an energy-harvesting array connected to a parallel storage network.

FIG. 7 is an electrical schematic of yet another energy-harvesting circuit 750 including an energy-harvesting array 756 with a corresponding matched circuit 752a-752d connected in parallel to a storage network (e.g., capacitor 753 and energy storage device 754). Storage network may be any suitable circuit capable of receiving and storing electrical energy from the energy-harvesting array 756 and matched circuits 752. In one embodiment, the storage network includes at least a capacitor and an energy storage device (e.g., one or more batteries 754). The storage network (e.g., capacitor 753 and energy storage device 754) connects to a voltage regulator 758 and the voltage regulator 758 generates a regulated voltage output $V_{DC}$.

An energy-harvesting circuit 350, 450 and 750, as illustrated in FIGS. 4, 5 and 7, and the control harvesting circuit 550, illustrated in FIG. 6, may be combined to form an energy and control harvesting circuit that harvests energy for generating a DC power signal and also harvests energy for detecting one or more control signals embedded in the electrosurgical energy signal by the electrosurgical generator 200.

As can be appreciated by the present disclosure, the electrical harvesting electrosurgical energy delivery system 30 utilizing an energy-harvesting system 260 according to one or more embodiments of the present disclosure provides only one physical connection (e.g., the transmission line 220 providing the electrosurgical energy signal) between the electrosurgical generator 200 and the energy-harvesting delivery device 210. The energy-harvesting delivery device 210 does not require direct connections for DC control power and/or control signals since DC control power to operate the energy-harvesting delivery device 210 is harvested from the electrosurgical energy signal (or other signals as discussed herein) and control information is passed through a wireless communication network 221 or harvested from the electrosurgical energy signal.

Isolation between the electrosurgical generator 200 and the patient (e.g., the energy-harvesting delivery device 210) is controlled by the isolation transformer 230 or other isolation device. As such, patient isolation, and therefore patient safety, is directly controlled by the isolation device, e.g., the isolation transformer 230.

In addition, the energy-harvesting system 260 may utilize a variety of one or more signals to harvest energy such as, for example, RF interference, ambient noise, system noise, undesirable harmonics, or any combination thereof, to generate power. As such, these undesirable signals actually increase the power available to the energy-harvesting delivery device 210.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical energy delivery apparatus, comprising:
   an energy delivery circuit configured to receive an electrosurgical energy signal via a transmission line from an electrosurgical energy source;
   a control circuit powered by the received electrosurgical energy signal and operatively connected to the energy delivery circuit, the control circuit configured to receive a control signal from an electrosurgical energy source and selectively enable a flow of electrosurgical energy from the energy delivery circuit to an energy delivery element based on the received control signal; and
   an energy-harvesting system including:
      a plurality of energy-harvesting circuits, each of the plurality of energy-harvesting circuits including:
         an energy-harvesting antenna configured to harvest energy from the received electrosurgical energy signal and generate an RF signal;
         a matched circuit operably coupled to the energy-harvesting antenna and configured to receive the RF signal from the energy-harvesting antenna, rectify the RF signal, and generate a DC signal; and
         an energy storage device configured to receive and store the DC signal; and
      a voltage regulator connected to the energy storage device and configured to provide a regulated DC voltage to power at least one of the energy delivery circuit or the control circuit.

2. The electrosurgical energy delivery apparatus according to claim 1, wherein the received electrosurgical energy signal has a primary frequency and at least one of the plurality of energy-harvesting circuits is tuned to the primary frequency.

3. The electrosurgical energy delivery apparatus according to claim 1, wherein the control circuit further includes:
   a communication circuit configured to provide a wireless connection between the control circuit and an electrosurgical energy source.

4. The electrosurgical energy delivery apparatus according to claim 1, wherein the received electrosurgical energy signal has a primary frequency and the plurality of energy-harvesting circuits are not tuned to the primary frequency.

5. The electrosurgical energy delivery apparatus according to claim 1, wherein the received electrosurgical energy signal has a primary frequency and the control signal is embedded within the received electrosurgical energy signal at a frequency different from the primary frequency.

6. An electrosurgical energy delivery apparatus comprising:
an energy delivery circuit configured to receive an electrosurgical energy signal via a transmission line from an electrosurgical energy source;
a control circuit powered by the received electrosurgical energy signal and operatively connected to the energy delivery circuit, the control circuit configured to receive a control signal from an electrosurgical energy source and selectively enable a flow of electrosurgical energy from the energy delivery circuit to an energy delivery element based on the received control signal; and
a control energy-harvesting system including:
a plurality of energy-harvesting circuits, each of the plurality of energy-harvesting circuits including:
an energy-harvesting antenna tuned to a particular frequency configured to harvest energy from the received electrosurgical energy signal and generate a RF signal;
a matched circuit operably coupled to the energy-harvesting antenna and configured to receive the RF signal from the energy-harvesting antenna, rectify the RF signal, and generate a DC signal; and
a switch controlled by the DC signal and configured to indicate that the energy-harvesting antenna is receiving the particular frequency,
wherein the switch indicates to the control circuit that the particular frequency was received by the energy-harvesting antenna.

7. The electrosurgical energy delivery apparatus according to claim 6, wherein the particular frequency of each of the plurality of energy-harvesting circuits is different.

8. The electrosurgical energy delivery apparatus according to claim 7, wherein the received electrosurgical energy signal has a primary frequency and the particular frequency of each of the plurality of energy-harvesting circuits is not equal to the primary frequency.

9. The electrosurgical energy delivery apparatus according to claim 8, wherein the received electrosurgical energy signal includes energy at a frequency equal to at least one of the particular frequencies of one of the plurality of energy-harvesting circuits.

10. The electrosurgical energy delivery apparatus according to claim 6, wherein the received electrosurgical energy signal includes energy at a frequency that corresponds to at least one of the particular frequencies of the plurality of energy-harvesting circuits.

11. The electrosurgical energy delivery apparatus according to claim 6, wherein the received electrosurgical energy signal has a primary frequency and the control signal is embedded within the received electrosurgical energy signal at a frequency different from the primary frequency.

12. An electrosurgical energy delivery apparatus, comprising:
an energy delivery circuit configured to receive an electrosurgical energy signal via a transmission line from an electrosurgical energy source;
a control circuit powered by the received electrosurgical energy signal and operatively connected to the energy delivery circuit, the control circuit configured to receive a control signal from an electrosurgical energy source and selectively enable a flow of electrosurgical energy from the energy delivery circuit to an energy delivery element based on the received control signal; and
an energy-harvesting system including:
a plurality of energy-harvesting circuits, each of the plurality of energy-harvesting circuits including:
an energy-harvesting antenna having a frequency range and configured to harvest energy from the received electrosurgical energy signal and generate an energy signal;
a matched circuit operably coupled to the energy-harvesting antenna and configured to receive the energy signal from the energy-harvesting antenna, the energy signal having energy at frequencies within the frequency range, the matched circuit configured to rectify the energy signal and generate a DC signal; and
an energy storage device configured to receive and store the DC signal; and
a voltage regulator connected to the energy storage device and configured to provide a regulated DC voltage to at least one of the energy delivery circuit or the control circuit.

13. The electrosurgical energy delivery apparatus according to claim 12, wherein at least one of the energy-harvesting antennas is a fractal antenna.

14. The electrosurgical energy delivery apparatus according to claim 12, wherein the control circuit further includes:
a communication circuit configured to provide a wireless connection between the control circuit and an electrosurgical energy source.

15. The electrosurgical energy delivery apparatus according to claim 12, wherein the received electrosurgical energy signal has a primary frequency and the plurality of energy-harvesting circuits are out of tune with the primary frequency.

16. The electrosurgical energy delivery apparatus according to claim 12, wherein at least one of the plurality of energy-harvesting circuits is configured to harvest energy from ambient electrical noise.

17. The electrosurgical energy delivery apparatus according to claim 12, wherein at least one of the plurality of energy-harvesting circuits is configured to harvest energy from an unregulated frequency.

18. The electrosurgical energy delivery apparatus according to claim 12, wherein at least one of the plurality of energy-harvesting circuits is configured to harvest energy from a regulated frequency.

19. The electrosurgical energy delivery apparatus according to claim 12, wherein the received electrosurgical energy signal has a primary frequency and the control signal is embedded within the received electrosurgical energy signal at a frequency different from the primary frequency.

* * * * *